US005472947A

United States Patent [19]

Saida et al.

[11] Patent Number: 5,472,947
[45] Date of Patent: Dec. 5, 1995

[54] APPLICATION OF 4-CARBAMOYL-1-β-D-RIBOFURANOSYL IMIDAZOLIUM-5-OLATE TO THE TREATMENT OF MULTIPLE SCLEROSIS

[75] Inventors: Takahiko Saida; Kyoko Saida, both of Kyoto, Japan

[73] Assignee: Asahi Kasei Kogyo Kabushiki Kaisha, Osaka, Japan

[21] Appl. No.: 281,613

[22] Filed: Jul. 28, 1994

Related U.S. Application Data

[63] Continuation of Ser. No. 90,699, Jul. 13, 1993, abandoned, which is a continuation of Ser. No. 849,808, Mar. 11, 1992, abandoned, which is a continuation of Ser. No. 701,864, May 17, 1991, abandoned.

[30] Foreign Application Priority Data

May 17, 1990 [JP] Japan ................................ 2-127529

[51] Int. Cl.$^6$ ................................ A61K 31/70
[52] U.S. Cl. .................... 514/43; 536/28.8; 514/903
[58] Field of Search ............... 514/43, 903; 536/28.8

[56] References Cited

U.S. PATENT DOCUMENTS

| | | | |
|---|---|---|---|
| 3,888,843 | 6/1975 | Mizuno et al. | 526/28.8 |
| 4,728,729 | 3/1988 | Tarumi et al. | 536/28.8 |

FOREIGN PATENT DOCUMENTS

| | | | |
|---|---|---|---|
| 0155164 | 9/1985 | European Pat. Off. | 514/43 |
| 48-056894 | 10/1973 | Japan | 536/28.8 |
| 50-121275 | 9/1975 | Japan | 536/28.8 |
| 50-121276 | 9/1975 | Japan | 536/28.8 |
| 51-001693 | 1/1976 | Japan | 536/28.8 |
| 57-156418 | 9/1982 | Japan | 514/43 |
| 60-142998 | 7/1985 | Japan | 514/43 |
| 7508706 | 1/1976 | Netherlands | 514/43 |

OTHER PUBLICATIONS

"Toyo Jozo Expanding Indicators of Existing Immunosuppressant and Developing New Immunoregulator," *The Chemical Daily(Japan)*, Feb. 26, 1991, p. 9.

Mizuno et al., "Studies on Bredinin. I. Isolation, Characterization and Biological Properties," *The Journal of Antibiotics*, 27(10), 775–782 (1974).

Hayashi et al., "Studies on Bredinin. III. Chemical Synthesis of Bredinin (A Novel Imidazole Nucleoside)," *Chem. Pharm. Bull.*, 23(1), 245–246 (1975).

"Symposium: [Review of the Status of Immunomodulating Therapies in Multiple Sclerosis]," *Neurology*, 38(Suppl. 2), pp. 4–89 (Jul., 1988).

Szobor et al., "Treatment of Multiple Sclerosis," *Ther. Hung.*, 37(2), 67–82 (1989).

Budavari et al. (eds.), *The Merck Index, 11th Ed.*, Merck & Co., Rahway, N.J., 1989, pp. 144, 431 and 980.

Berkow et al. eds. *The Merck Manual of Diagnosis and Therapy*, Merck Research Laboratories, Rahway, N.J., 1992, pp. 1487–1490.

Yudkin et al., "Overview of Azathioprine Treatment in Multiple Sclerosis," *The Lancet*, 338, 1051–1055 (1991).

R. A. C. Hughes et al., "Double–masked Trial of Azathioprine in Multiple Sclerosis," *The Lancet*, 1988, 179–183.

Milanese et al., "Double Blind Controlled Randomized Study on Azathioprine Efficacy in Multiple Sclerosis. Preliminary Results," *Ital. J. Neurology*, 9, 53–57 (1988).

Ellison et al., "A Placebo–controlled, Randomized, Double–masked, Variable Dosage, Clinical Trial of Azathioprine With and Without Methylprednisolone in Multiple Sclerosis," *Neurology*, 39, 1018–1026 (1989).

*Primary Examiner*—Douglas W. Robinson
*Assistant Examiner*—L. Eric Crane
*Attorney, Agent, or Firm*—Young & Thompson

[57] ABSTRACT

A composition for the treatment or prevention of multiple sclerosis is disclosed. It comprises mizoribine (4-carbamoyl-1-β-D-ribofuranosyl imidazolium-5-olate) as the effective component. It is a safe drug, exhibiting a minimal degree of side-effects, and thus can be administered over a long period of time. Administration of the drug, usually 1–20 mg/kg (body weight) per day for adults, improves the functional disturbances of multiple sclerosis.

3 Claims, No Drawings

APPLICATION OF 4-CARBAMOYL-1-β-D-RIBOFURANOSYL IMIDAZOLIUM-5-OLATE TO THE TREATMENT OF MULTIPLE SCLEROSIS

This application is a continuation of application Ser. No. 08/090,699, filed Jul. 13, 1993 now abandoned, which is a continuation of application Ser. No. 07/849,808, filed Mar. 11, 1992 now abandoned, which is a continuation of application Ser. No. 07/701,864, filed May 17, 1991, now abandoned.

BACKGROUND OF THE INVENTION

1. Field of the Invention

The present invention relates to a composition for the treatment or prevention of multiple sclerosis comprising 4-carbamoyl-1-β-D-ribofuranosyl imidazolium-5-olate.

2. Description of the Background Art

Multiple sclerosis is a disease involving temporary and multiple disorders in the central nervous system; i.e., disorders in the medullary sheath of the brain, the spinal, and the visual nerve, producing polydomous demyelinating lesions. The disease is clinically found in young adults, and disorders are found in more than one site in the central nervous system, with repeated relapsing and remission. In many cases the initial symptom is decreased visual acuity, followed by motor paralysis, paralysis, gait disturbance, hyperesthesia, double vision, and speech disorder [Encyclopedia of Medical Sciences, 31, 53–54 (1982)].

The criterion defined by Multiple Sclerosis Research Team, the Ministry of Health and Welfare, Japan, in 1989 is as follows. (1) At least two lesions are found in the central nervous system, diagnosed based on the symptoms and the views obtained by physical examinations, (2) the relapsing and remission are repeated, and (3) disturbances in the nervous system due to other diseases (e.g cerebrovascular disease, hemangioma, HTLV-I-associated myelopathy, collagen disease, Behget disease, syringomyelia, spino-cerebullar degeneration, cerevical vertebral myelopathy, subacute myelo-optico-neuropathy, syphilis, etc.) are recognized. The diseases completely satisfying all of the above 3 items are deemed the multiple sclerosis confirmed by the clinically diagnosis. Optic neuromyelitis (Devic disease) is considered to be a type of multiple sclerosis.

Although certain immunological disturbances are recognized in multiple sclerosis, the true cause of the disease still remains to be elucidated. For this reason, there are no currently established treatments for the cure of multiple sclerosis. Some reports describe that administration of certain steroid compounds is effective for gradually releasing the symptoms in the acute stage, e.g. administration of dexamethasone, initially about 6 mg/day and gradually decreasing the dose while observing the symptoms, or administration of 20–40 units/dayof ACTH (adrenocorticotrophic hormone) [*Neurology*, 38(7) 4–89 (1988)]. Other measures proposed for the treatment of multiple sclerosis are rehabilitation during recovery stage, administration of baclofen or dantrolene as a muscle relaxant for decreasing spasticity, or administration of carbamazepine as an anticonvulsant for treating painful tonic seizure. Avoiding strain, common cold, viral infection, and psychic stress are also proposed as measures for the prevention of the relapsing.

However, the most frequently used steroid compounds had a problem of causing serious side-effects such as moon face, cushing syndrome infection, and osteoporosis. The occurrence of side-effects is particularly problematic in the treatment of multiple sclerosis which needs long-term administration of the drugs.

The development of a drug for curing multiple sclerosis which is safe with least side-effects and can be administered to the patients over a long period of time was therefore urgently desired.

SUMMARY OF THE INVENTION

In view of this situation, the present inventors have undertaken extensive studies on the efficacy and the safety of various compounds possibly useful against multiple sclerosis, and found that 4-carbamoyl-1-β-D-ribofuranosyl imidazolium-5-olate which is known as an immnosuppressant is effective for multiple sclerosis and safe with minimal side-effects and can be administered to the patients over a long period of time. Such a finding has led to the completion of the present invention.

Accordingly, an object of this invention is to provide a composition for the treatment or prevention of multiple sclerosis comprising 4-carbamoyl-1-β-D-ribofuranosyl imidazolium-5-olate and pharmaceutically acceptable carriers.

Other objects, features and advantages of the invention will hereinafter become more readily apparent from the following description.

DETAILED DESCRIPTION OF THE INVENTION AND PREFERRED EMBODIMENTS

4-Carbamoyl-1-β-D-ribofuranosyl imidazolium-5-olate which is the effective component of the composition of the present invention is a nucleic acid-related compound discovered in the culture broth of *Eupenicillium brefeldianum*M-2116, a microorganism belonging to the genus *Eupenicillium*. The compound is generally called mizoribine. It is a weakly acidic substance which is readily soluble in water and decomposes producing brown foam at about 200° C. Various processes are known for producing mizoribine, e.g. *J. Antibiotics*, 27, (10) 775 (1974), *Chem. Pharm. Bull.*, 23, 245 (1975), Japanese Patent Laid-open (ko-kai) Nos. 56894/1973, 1693/1976, 121275/1975, 121276/1975, and the like.

4-Carbamoyl-1-β-D-ribofuranosyl imidazolium-5-olate (hereinafter referred to as mizoribine) possesses an immunosuppressing activity; e.g. its efficacy in suppressing rejection reactions in kidney transplant is known. Tablets of its anhydrous crystals are sold under the trademark of Bredinin (a product of Toyo Jozo Co., Ltd.). The drug is administered in an amount of 2–3 mg/kg/day as an initial dose and 1–2 mg/kg/day as a maintenance dose.

Mizoribine is an extremely safe compound, exhibiting very low acute toxicity as shown in Tables 1 and 2.

TABLE 1

| | $LD_{50}$ (mg/kg) in Mouse | | | |
|---|---|---|---|---|
| | Manner of Administration | | | |
| | Orally (p.o.) | Subcutaneously (s.c.) | Intravenously (i.v.) | Intramuscularly (i.m.) |
| Male | >4883 | >4883 | >3042 | >2800 |
| Female | >4883 | >4883 | >3042 | >2800 |

TABLE 2

| | LD$_{50}$ (mg/kg) in Rat | | | |
|---|---|---|---|---|
| | Manner of Administration | | | |
| | Orally (p.o.) | Subcutaneously (s.c.) | Intravenously (i.v.) | Intramuscularly (i.m.) |
| Male | >3100 | >4161 | >2572 | >2800 |
| Female | >2847 | >3795 | >2608 | >2800 |

Mizolibine can be administered orally, intravenously, subcutaneously, or intrarectally for the treatment of multiple sclerosis. Oral administration is desirable considering the use of the drug over a long period of time. The preparation for the oral administration may be in the form of capsules, granules, powders, tables, or the like. The mizoribine tablets already sold on the market is conveniently used. Such preparations for the oral administration can be prepared by incorporating suitable carriers and additives such as excipients, binders, disintegrators, lubricants, coating agents, coloring agents, flavoring agents, corrigants, plasticizers, and the like.

A dose of mizoribine of the present invention is usually 1–20 mg/kg (body weight) per day for adults. A preferable manner of the administration, for example, to an adult patient with a body weight of 50–60 kg is dosing 25 mg or 50 mg mizoribine tablets, 100 mg one time and three times a day. The term of the administration may be from 5 months to several years depending on the symptoms of the patient.

The administration of mizoribine improves the functional disturbances of multiple sclerosis patients and prevents the relapse. It exhibits a minimal degree of side-effects, is safe and can be administered over a long period of time.

Other features of the invention will become apparent in the course of the following description of the exemplary embodiments which are given for illustration of the invention and are not intended to be limiting thereof.

EXAMPLES

Example 1

Mizoribine (BREDININ 50: trademark, a product of Toyo Jozo Co., Ltd.) was administered to 10 subjects who were recognized as suffering from multiple sclerosis and classified according to the clinical types into RR-type (subjects with repeated relapsing and remission) and RR-CP-type (subjects changing to the chronically progressive type from RR-type). The dose and the period of the administration, shown in Table 3, were determined according to the types and other factors. The effects of the treatment were evaluated in terms of the Krutzke's expanded DDS;EDSS, the functional system, and the exacerbation frequency, each of which is defined below.

(a) Krutzke's expanded DDS (EDSS)

Motion and walking capability are the major items of judgment. The results are classified into 20 scores according to the grades 0 to 10, defined in *Neurology*, 33, 1444–1452 (1983).

(b) Functional System (FS)

The disorders were classified into those in the pyramidal tract, cerebellum, brainstem, sensation, bladder, rectum, visual capability, and mental capacity. Their functions were rated on a 6 point scale from 0 to 5 according to *Neurology*, 33, 1444–1452 (1983).

(c) Exacerbation Frequency

A neurological symptom considered to be caused by the multiple sclerosis and lasting longer than one day was scored as one exacerbation.

The results are shown in Table 3.

TABLE 3

| Subject | Age | Sex | Clinical Type | Initial State of Disease[1] | Period of Disease[2] | Period of Treatment[3] | Dose[4] Initial | Dose[4] Current | EDSS Before | EDSS After | FS Before | FS After | Exacerbation Frequency Before[5] | Exacerbation Frequency After[5] |
|---|---|---|---|---|---|---|---|---|---|---|---|---|---|---|
| 1 | 26 | M | RR | A | 7 | 13.0 | 6/0.5 | 4/0.4 | 6 | 6 | 15 | 13 | 0 | 0 |
| 2 | 50 | F | RR | A | 8 | 12.0 | 4/0.4 | 4/0.4 | 7.5 | 7.5 | 16 | 16 | 1 | 0 |
| 3 | 41 | F | RR | B | 2 | 10.0 | 6/0.5 | 4/0.4 | 7 | 7 | 13 | 10 | 0.5 | 3.6 |
| 4 | 34 | F | RR | A | 3 | 13.0 | 6/0.5 | 4/0.4 | 6.5 | 6 | 16 | 15 | 1.5 | 0 |
| 5 | 39 | M | RR | B | 8 | 11.0 | 4/0.4 | 4/— | 2 | 0 | 6 | 2 | 2 | 0 |
| 6 | 36 | M | RR-CP | B | 6 | 12.0 | 6/0.5 | 4/0.4 | 6.5 | 4 | 14 | 7 | 1 | 2 |
| 7 | 32 | M | RR | A | 2 | 13.0 | 6/0.5 | 4/0.4 | 5 | 3.5 | 11 | 9 | 2 | 0 |
| 8 | 43 | M | RR-CP | B | 5 | 12.0 | 6/0.5 | 4/0.4 | 7.5 | 7 | 20 | 19 | 0 | 0 |
| 9 | 58 | F | RR | B | 11 | 6.0 | 4/0.4 | 4/0.4 | 7 | 7 | 7 | 7 | 1.2 | 0 |
| 10 | 30 | F | RR | A | 4 | 6.0 | 4/0.4 | 4/0.4 | 7 | 7 | 7 | 7 | 1 | 0 |

[1]Initial State of Disease A: Under remission, B: Under exacerbation
[2]Period of disease: year
[3]Period of treatment: month
[4]Dose; Mizolibine/methylprednisolone: mg/kg/day
[5]Exacerbation frequency during 1 year The results shown in Table 3 shows that the administration of mizoribine was recognized to improve the symptoms or to suppress the progress of the disease in the patients with multiple sclerosis of both clinical types; RR and RR-CP. No side-effects were observed during the period of the administration.

Example 2

| | |
|---|---|
| Mizoribine (anhydrous crystals) | 50 mg |
| Anhydrous lactose | 126 mg |
| Crystalline cellulose | 20 mg |
| Carboxymethyl cellulose (as Ca) | 10 mg |
| Magnesium stearate (as Mg) | 2 mg |

The above components were mixed and granulated. Magnesium stearate was added to the granule and the mixture was made into tablets each weighing 210 mg (mizoribine content: 50 mg). The tablets can be served as an agent for the prevention or treatment of multiple sclerosis.

Since mizoribine is safe with no substantial side-effects, it can be used for a long period of time. It is a useful agent for preventing the relapsing or improving the disturbance due to multiple sclerosis.

Obviously, numerous modifications and variations of the present invention are possible in light of the above teachings. It is therefore to be understood that within the scope of the appended claims, the invention may be practiced otherwise than as specifically described herein.

What is claimed is:

1. A method of treating multiple sclerosis which comprises administering an effective amount of 4-carbamoyl-1-β-D-ribofuranosyl imidazolium-5-olate to a patient suffering from multiple sclerosis.

2. A method according to claim 1, wherein the administation of 4-carbamoyl-1-β-D-ribofuranosyl imidazolium-5-olate is by the oral route.

3. A method according to claim 1, wherein said effective amount is 1–20 mg/kg body weight per day.

* * * * *

UNITED STATES PATENT AND TRADEMARK OFFICE
CERTIFICATE OF CORRECTION

PATENT NO. : 5,472,947  Page 1 of 2
DATED : December 5, 1995
INVENTOR(S) : Takahiko SAIDA et al.

It is certified that error appears in the above-indentified patent and that said Letters Patent is hereby corrected as shown below:

On the title page, in Item [54], change "OLATE" to --OLEATE--;

in Item [57], line 3, change "olate)" to --oleate)--.

Column 1, line 3, change "OLATE" to --OLEATE--;

line 18, change "olate." to --oleate.--.

Column 2, line 16, change "olate" to --oleate--;

line 24, change "olate" to --oleate--;

line 33, change "olate" to --oleate--;

line 46, change "olate" to --oleate--.

UNITED STATES PATENT AND TRADEMARK OFFICE
CERTIFICATE OF CORRECTION

PATENT NO. : 5,472,947
DATED : December 5, 1995
INVENTOR(S) : Takahiko SAIDA et al.

It is certified that error appears in the above-indentified patent and that said Letters Patent is hereby corrected as shown below:

Column 6, line 4, (claim 1, line 3), change "olate" to --oleate--;

line 8, (claim 2, line 3), change "olate" to --oleate--.

Signed and Sealed this

Thirteenth Day of May, 1997

*Attest:*

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO.   : 5,472,947

DATED        : December 5, 1995

INVENTOR(S)  : Takahiko Saida et al

It is certified that error appears in the above-identified patent and that said Letters Patent is hereby corrected as shown below:

On the title page, in item [54], change "OLEATE" to --OLATE--; and in item [57], line 3, change "oleate)" to --olate)--.

Column 1, line 3, change "OLEATE" to --OLATE--;
           line 18, change "oleate." to --olate.--.
Column 2, line 16, change "oleate" to --olate--;
           line 24, change "oleate" to --olate--;
           line 33, change "oleate" to --olate--;
           line 46, change "oleate" to --olate--.
Column 6, line 4, (claim 1, line 3), change "oleate" to --olate--;
           line 8, (claim 2, line 3), change "oleate" to --olate--.

This certificate supercedes the certificate of correction issued May 13, 1997.

Signed and Sealed this

Twenty-ninth Day of July, 1997

Attest:

BRUCE LEHMAN

Attesting Officer

Commissioner of Patents and Trademarks